United States Patent [19]

Baker

[11] Patent Number: 5,338,315
[45] Date of Patent: Aug. 16, 1994

[54] COLOSTOMY PROTECTION DEVICE

[76] Inventor: Freddie R. Baker, 2104 Rose Cliff Dr., Nashville, Tenn. 37206

[21] Appl. No.: 831,472

[22] Filed: Apr. 28, 1992

[51] Int. Cl.⁵ .............................................. A61F 5/44
[52] U.S. Cl. .................................. 604/395; 604/340; 128/888
[58] Field of Search ................ 128/846, 876, 888; 604/338, 340, 343, 345, 337, 332

[56] References Cited

U.S. PATENT DOCUMENTS

| | | | |
|---|---|---|---|
| 695,761 | 3/1902 | Peacock | 128/888 |
| 1,922,763 | 8/1933 | Gricks | 604/340 |
| 2,652,827 | 9/1953 | Smith | 128/846 |
| 2,788,785 | 4/1957 | Present | 604/345 |
| 3,026,874 | 3/1962 | Stevens | 128/888 X |
| 3,674,032 | 7/1972 | Minganti | 128/846 X |
| 3,722,508 | 3/1973 | Roberts | 128/888 X |
| 5,048,512 | 9/1991 | Turner et al. | 604/345 X |
| 5,072,738 | 12/1991 | Wonder et al. | 128/846 X |
| 5,135,519 | 8/1992 | Helmer | 604/345 X |

Primary Examiner—Robert A. Hafer
Assistant Examiner—Sam Rimell
Attorney, Agent, or Firm—Rick R. Wascher; Casey F. Wilson

[57] ABSTRACT

A device for use by a person wearing a colostomy, ileostomy or ureterostomy bag which protects the bag from binding by clothes and being noticed as readily by others. The device is a semirigid guard worn by the person below the stoma at the level of his or her waistband or belt line. The inner portion of the guard conforms to fit snugly and comfortably against the person's body. The outer portion of the guard is semirigid and curved to permit the waistband of the person's clothing to fit smoothly around the guard. The inner and outer portions may be separate pieces, removably attached to one another, as with hook and loop fasteners. Between the inner and outer portions of the guard is an opening through which the bag hangs freely. The outer portion may extend up to a level so that it covers and protects the stoma.

10 Claims, 6 Drawing Sheets

COLOSTOMY PROTECTION DEVICE

BACKGROUND OF THE INVENTION

Colostomies and colostomy bags are quite well known, and obviously are of great benefit to those who require them. One inconvenience frequently encountered by one wearing a colostomy bag is that one's clothing may bind the colostomy bag, interfering with its ability to properly and completely fill. A second inconvenience is that the stoma—the point of connection between the person's body and the colostomy bag—may be irritated by the rubbing of clothing, seat belts, etc., against the connection during the course of a day's activities. Similar situations are involved with the use of ureterostomy bags.

Garments which hold colostomy or ureterostomy bags are known in the art. However, these garments are not rigid and do not protect the bag and the stoma as does the present invention. Examples of such garments can be found in the following U.S. patents:

| | | |
|---|---|---|
| 2,476,513 | Scott | July 19, 1949 |
| 2,503,056 | Lay | Apr. 4, 1950 |
| 2,778,362 | Pollock et al | Jan. 22, 1957 |
| 2,788,785 | Present | Apr. 16, 1957 |
| 3,421,505 | Freeman et al | Jan. 14, 1969 |
| 3,468,310 | Kimball | Sep. 23, 1969 |
| 4,495,662 | Miller | Jan. 29, 1985 |
| 4,533,355 | Fair | Aug. 6, 1985 |
| 4,888,006 | Beaupied | Dec. 19, 1989 |
| 5,026,362 | Willett | June 25, 1991 |

SUMMARY OF THE INVENTION

This invention is a device to be worn by a person with a ileostomy, colostomy or ureterostomy bag. Examples and embodiments given herein will be for ileostomy bags, but are applicable to colostomy and ureterostomy bags. The invention is intended to reduce or eliminate binding and constriction of the bag by the person's clothing, and to reduce or eliminate noticeable changes in the person's appearance to others. In certain embodiments the invention is intended to reduce or eliminate irritation of the stoma caused by rubbing, contact, movement, etc.

The invention is a semirigid guard worn by the person below the stoma. The inner portion of the guard is curved to fit snugly and comfortably against the person's body. The outer portion of the guard is similarly curved to permit the waistband of the person's clothing to fit smoothly around the guard and to minimize its effect upon the person's appearance The inner and outer portions may be separate pieces, removably attached to one another, as with hook and loop fasteners. Between the inner and outer portions of the guard is an opening through which the colostomy bag hangs freely. The pressure of the person's clothing at the waistband is borne by the guard rather than the colostomy bag. Further, as the colostomy bag fills, because it hangs freely through the guard, it does not create additional bulges beneath the person's clothing.

Different sizes and shapes may be used for the outer portion. A small outer portion may be used when wishes the guard to be relatively unobtrusive. A larger outer portion may be used. Such a larger outer portion extends upward and shields the stoma. The bag may be attached to the inside of the guard, allowing the guard to bear the weight of the bag. This attachment may be accomplished by means of hook and loop fasteners.

DESCRIPTION OF THE PREFERRED EMBODIMENT

Figure 1:
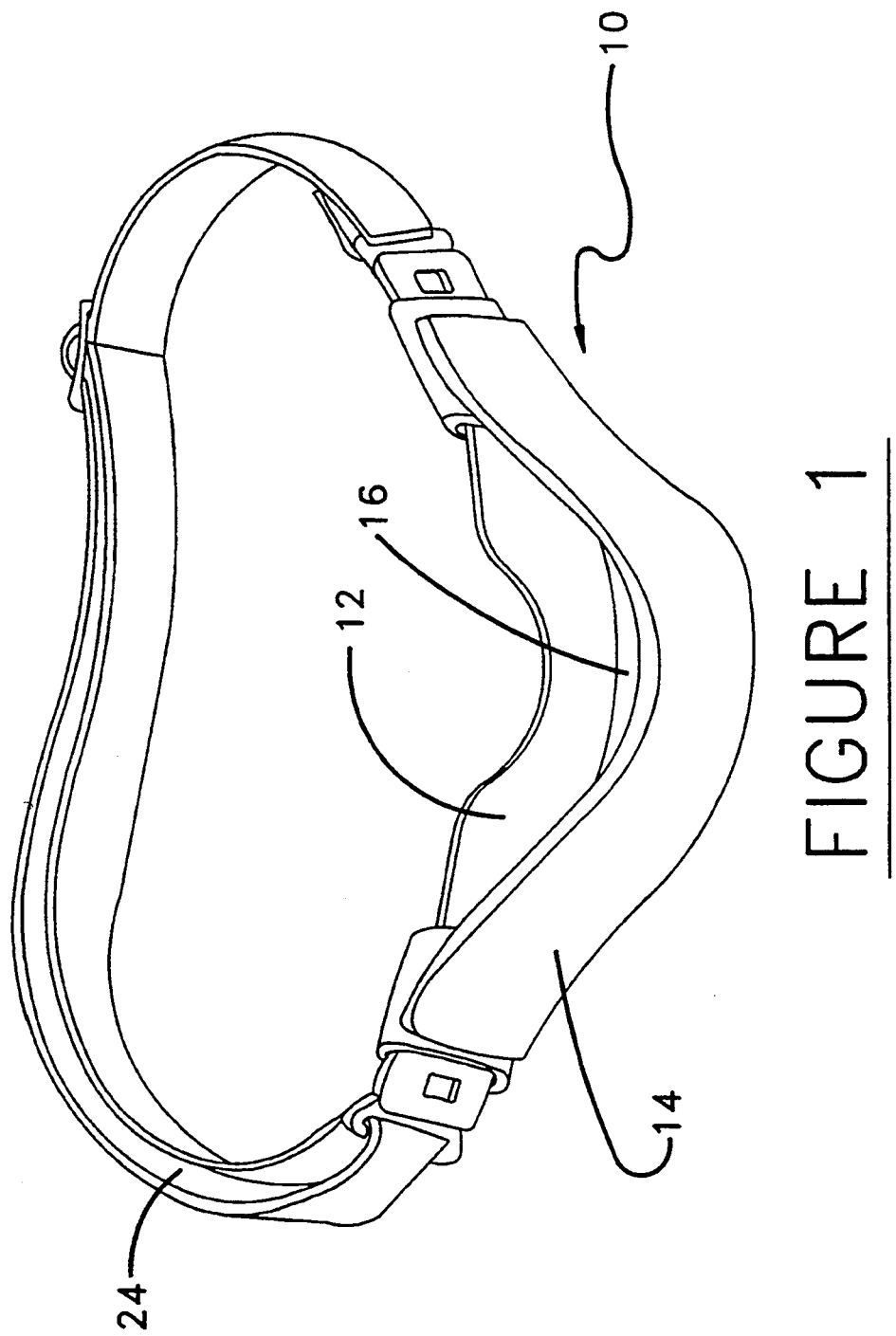
FIG. 1 is an elevated perspective view of an embodiment of the present invention.
Figure 2:
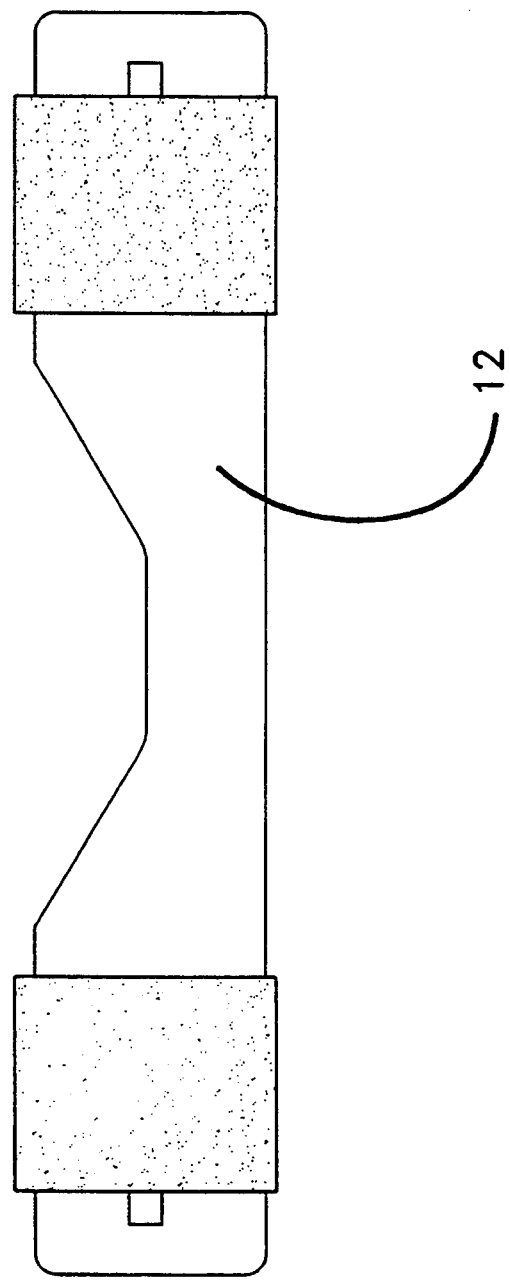
FIG. 2 is a front view of a portion of the invention shown in FIG. 1.
Figure 3:
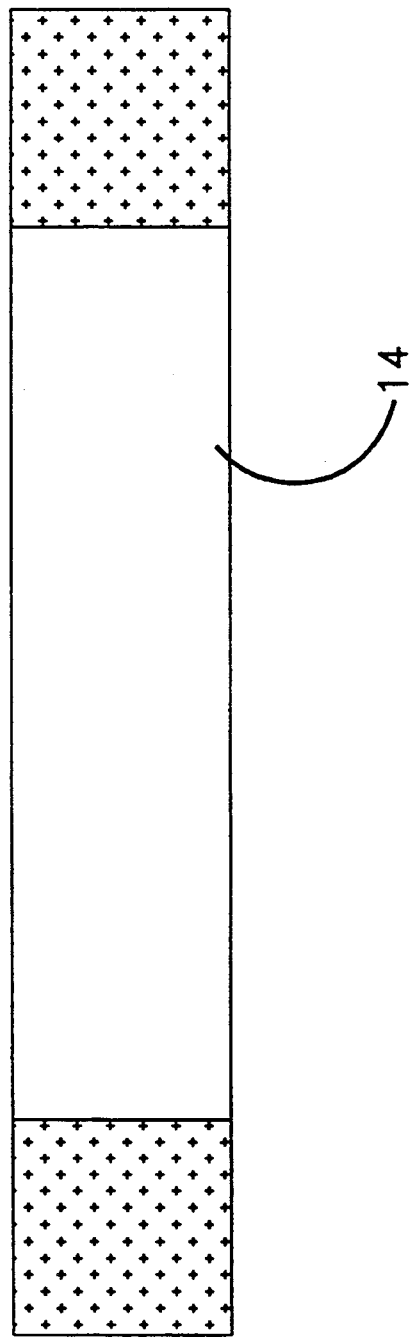
FIG. 3 is a rear view of an outer portion of the embodiment of the present invention shown in FIG. 1.
Figure 4:
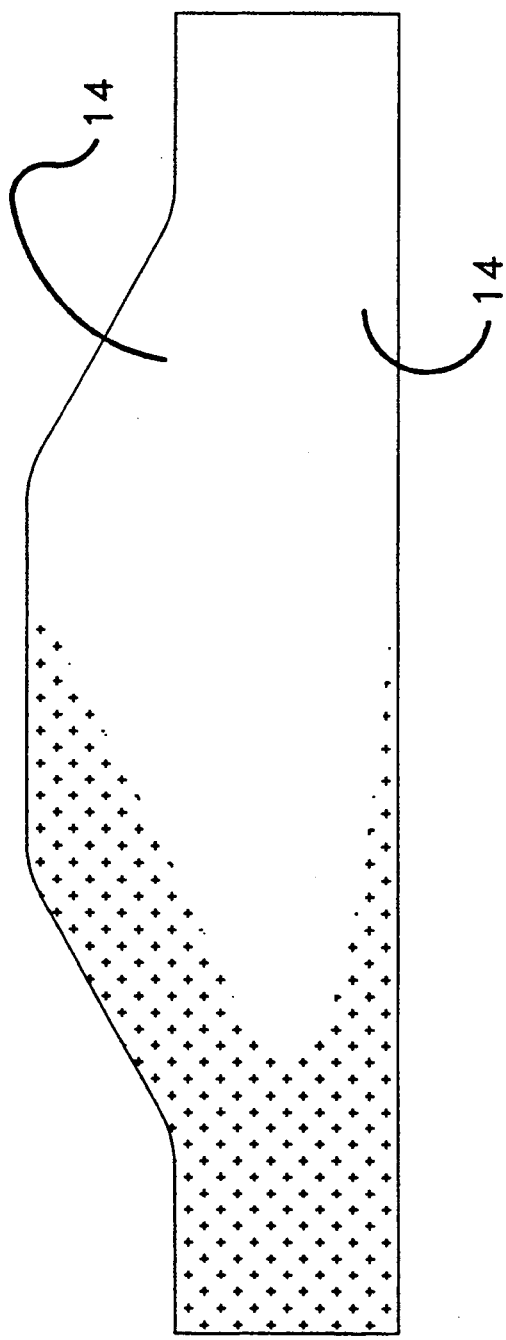
FIG. 4 is an alternate embodiment of the outer portion shown in FIG. 3.
Figure 5:
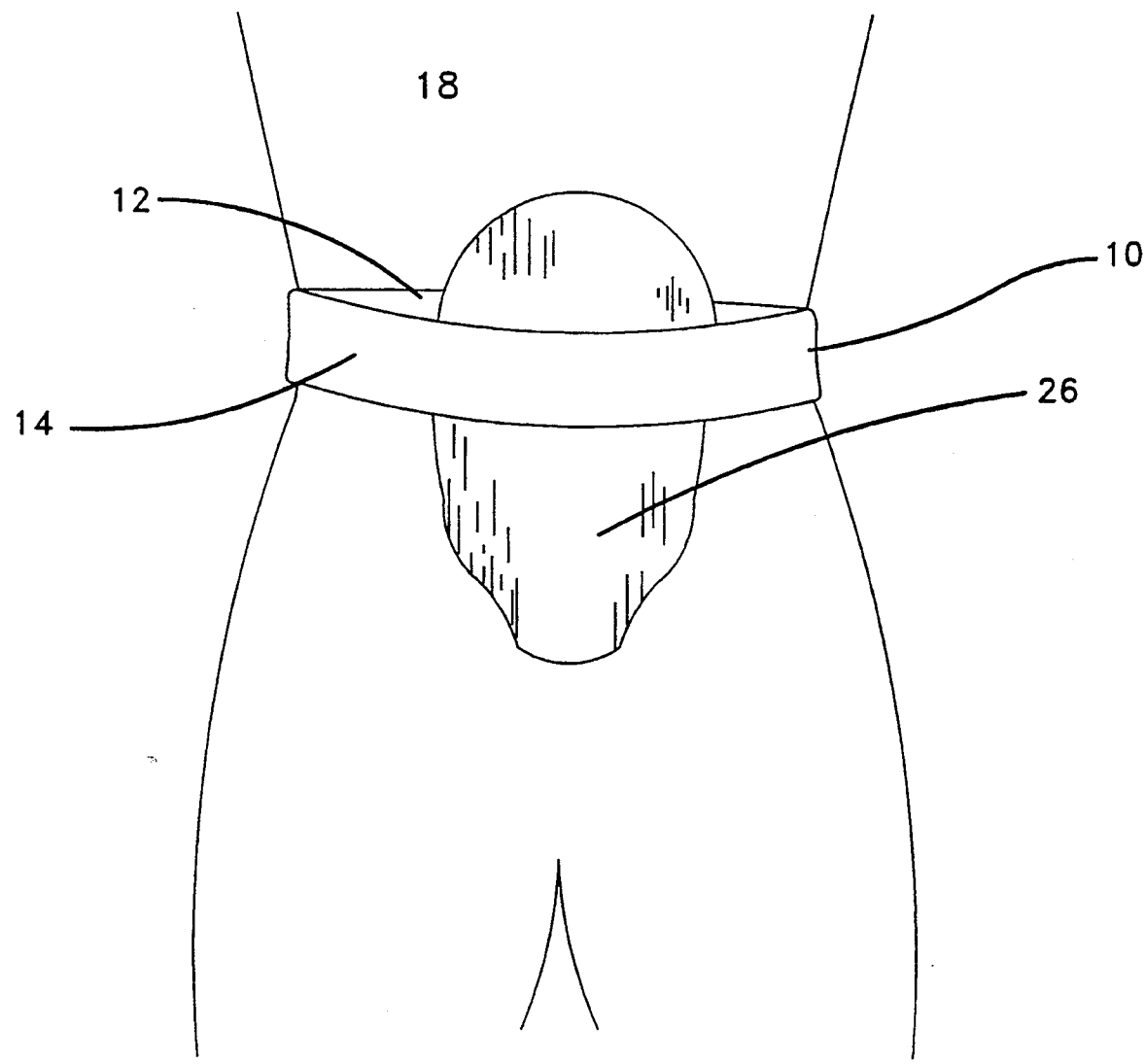
FIG. 5 is a perspective view of an embodiment of the present invention shown operably positioned on the human body.
Figure 6:
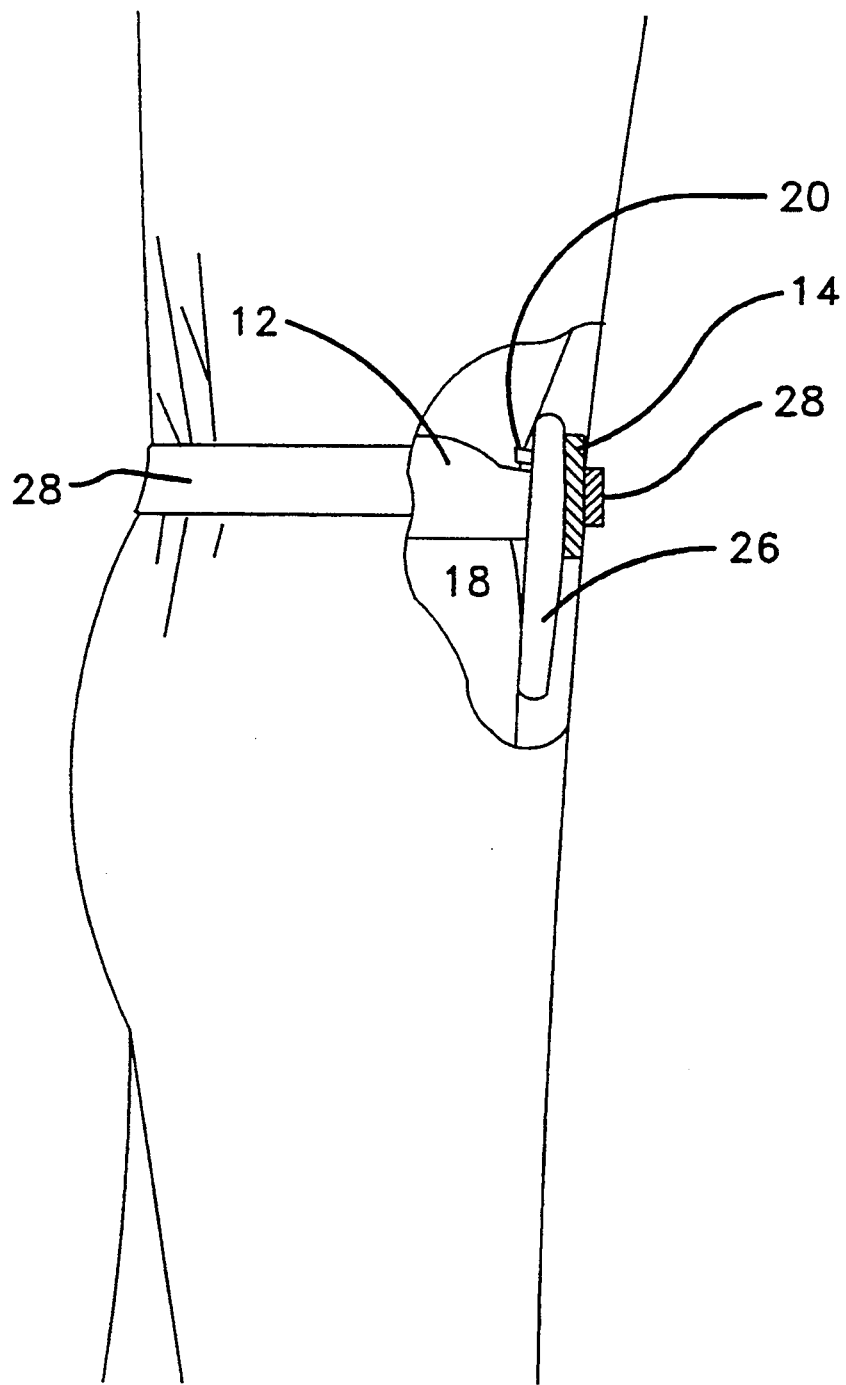
FIG. 6 is a partial cutaway view of an embodiment of the present invention shown operably positioned on the human body and with portions removed to show the relative alignment of the components thereof.

Referring with particularity to the figures, a device made in accordance with this invention is shown. A guard 10 has an inner portion 12 and an outer portion 14. An opening 16 extends vertically through the guard 10, between the inner and outer portions 12 and 14. The inner portion 12 is made of a semirigid material, such as a plastic, which conforms to the person's body 18. The outer portion 14 also is constructed of a semirigid material. The inner and outer portions 12 and 14 are removably attached at their ends, as with hook and loop fasteners.

The guard 10 is worn on a person's body 18 below the stoma 20. A convenient way to wear the guard 10 is such that the waistband of the person's clothing fits around the outer portion 14. The outer portion 14 may be provided with a material which will engage the person's clothing to assist in holding the clothing is position on the guard 10 The guard 10 is secured to the person's body 18 by suitable means. The preferred method is an elastic strap 24 wrapped around the person's body 18 and attached to the guard 10 at both ends. The colostomy bag 26 hangs freely through the opening 16 in the guard 10. The person can then don his or her clothes, placing them over the bag 26 and guard 10. The waistband 28 of the clothing is worn around the outer portion 14 of the guard 10. When used in this way the guard 10 prevents the person's clothing from binding or constricting the bag 26. Further, as the bag 26 fills it does not press against the person's clothing because the clothing is held away from the bag 26 by the guard 10.

The bag 26 may be attached to the inside of the guard 10, as with hook and loop fasteners. The inside of the outer portion 14 is covered with the hook material, and a strip of the mating loop material attached to the bag.

The outer portion 14 may have an extended vertical length as shown in FIG. 1. Such an outer portion 14 protects the stoma 20.

The embodiments of the invention described above are examples of possible embodiments. Modifications in and changes to the embodiments described will be apparent, and are within the scope and spirit of the invention as claimed.

I claim:

1. A device for an ostomy bag connection to a person's body at a stoma, said device comprising:

(a) a guard worn on said person's body below said stoma, said guard having a first side component having spaced apart end portions, a front surface, a back surface, a top edge, and a bottom edge, wherein said front surface of said first component faces away from said person's body, and said back surface is adjacent said person's body a second side component, opposite said first side component, and having spaced apart end portions, a front surface, and a back surface, wherein said front surface of said second component faces away from said person's body and said back surface of said second side component faces toward said front surface of said first side component, attachment means, between said first side component and said second side component, for removable attaching said back surface of said second side component at said spaced apart end portions of said second side component, to at least a portion of said front surface of said first side component at aid spaced apart ends of said first side component, enabling said second side component to be removable attached to said first side component, a vertical opening extending between said first side component and second side component sufficiently large to permit said bag to hand therethrough, and (b) securing means, attached to said spaced apart ends of said first side component, for detachably securing said guard on said person's body, and said top edge of said first side component has a cutaway portion in association with said top edge thereof enabling said ostomy bag to easily overlie said top edge at said cutaway portion.

2. The device of claim 1 wherein said means for securing is a strap connected to said guard and placed around said person's body.

3. The device of claim 1 wherein said second side extends generally vertically to an upper end, said upper end being above said stoma.

4. The device of claim 1 wherein:

said second side component attached to said first side component is configured to enable said back surface of said second side component to abut said ostomy bag adjacent said stoma.

5. A protector for an ostomy bag worn on the person in the region of a stoma, comprising:

(a) a first body component having spaced apart end regions, a front surface, a back surface, a top edge, and a bottom edge;

(b) a second body component removably attached to said first body component and having spaced apart end regions, a front surface and a back surface;

wherein the attached combination of said first body component and said second body component forms an ostomy bag receiving space to receive an ostomy bag;

(c) attachment means associated with either of said first body component and said second body component for securing the combination of said first and second body components to the person of the wearer, and;

(d) said top edge of said first body component has a cutaway portion in association with said top edge thereof enabling said ostomy bag to easily overlie said top edge at said cutaway portion.

6. The protector of claim 5, wherein:

said first body component is contoured such that said back surface will conform to the shape of the wearer.

7. The protector of claim 5, wherein:

said second body component is contoured such that said receiving space is formed from the combination of the contours of said first body component and said second body component.

8. The protector of claim 5, wherein said attachment means comprises:

belt means engageable with either of said first body component and said second body component for encircling the person of the wearer enabling the combination of said first and second body components to be secured thereto.

9. The protector of claim 8, wherein:

said belt means is an elastic strap.

10. The protectors of claim 5 wherein:

said second body component attached to said first body component is configured to enable said back surface of said second body component to abut said ostomy bag adjacent said stoma.

* * * * *